(12) United States Patent
Tokarski et al.

(10) Patent No.: US 6,768,010 B1
(45) Date of Patent: Jul. 27, 2004

(54) ORGANOPHOTORECEPTOR WITH AN EPOXY-MODIFIED CHARGE TRANSPORT COMPOUND HAVING AN AZINE GROUP

(75) Inventors: Zbigniew Tokarski, Woodbury, MN (US); Nusrallah Jubran, St. Paul, MN (US); Vytautas Getautis, Kaunas (LT); Maryte Daskeviciene, Jonava (LT); Edmundas Montrimas, Vilnius (LT); Valentas Gaidelis, Vilnius (LT)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 10/663,970

(22) Filed: Sep. 16, 2003

(51) Int. Cl.$^7$ .......................... C07D 209/86; G03G 5/00
(52) U.S. Cl. ................... 548/444; 546/100; 549/551; 430/58.45; 430/78; 430/79
(58) Field of Search .................... 548/444; 549/100, 549/551; 430/58.45, 78, 79

(56) References Cited

U.S. PATENT DOCUMENTS

| | | | |
|---|---|---|---|
| 4,297,426 A | | 10/1981 | Sakai et al. |
| 4,786,571 A | | 11/1988 | Ueda |
| 5,098,810 A | * | 3/1992 | Mizuguchi et al. ........... 430/78 |
| 6,670,085 B2 | * | 12/2003 | Jubran et al. ............. 430/58.6 |

FOREIGN PATENT DOCUMENTS

| | | |
|---|---|---|
| GB | 816923 | 7/1959 |
| JP | 62116943 | 5/1987 |
| JP | 2001-166519 | 6/2001 |

OTHER PUBLICATIONS

P.M. Thangamathesvaran and S.R. Jain, "Synthesis, Characterization And Binding Properties Of Epoxy Resins Based On Carbonohydrazones And Thiocarbonohydrazones," Frontiers of Polymer Research, p. 589–594, Edited by P.N. Prasad and J.K. Nigam, Plenum Press, NY, 1991.

S.R.Jain et al, "Novel Energetic N–N Bonded Polymeric Binders for Composite Propellants," Macromolecules New Frontiers, p. 1018–1021, Allied Publishers Ltd., New Delhi, 1998.

* cited by examiner

*Primary Examiner*—Fiona T. Powers
(74) *Attorney, Agent, or Firm*—Patterson, Thuente, Skaar & Christensen, P.A.

(57) ABSTRACT

Organophotoreceptors comprise an electrically conductive substrate and a photoconductive element on the electrically conductive substrate, the photoconductive element comprising:

a) a charge transport compound having the formula

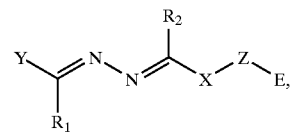

where $R_1$ and $R_2$ are, independently, hydrogen, an alkyl group, a heterocyclic group, an alkaryl group or an aryl group; X is an aromatic group; Y is an (N,N-disubstituted) arylamine group, such as a (N,N-disubstituted) arylamine group, a carbazole group or a julolidine group; Z is $(CH_2)_m$ group where m is an integer between 1 and 30 where one or more of the methylene groups is optionally replaced by O, S, C=O, O=C—O, O=C—$NR_3$, sulfoxide, sulfate, phosphate, an aryl group, urethane, urea, a $NR_4$ group, a $CHR_5$ group, or a $CR_6R_7$ group where $R_3$, $R_4$, $R_5$, $R_6$, and $R_7$ are, independently, H, hydroxyl, thiol, an amine group, an alkyl group, a heterocyclic group, an alkaryl group, or an aryl group; and E is an epoxy group; and b) a charge generating compound.

30 Claims, No Drawings

ORGANOPHOTORECEPTOR WITH AN EPOXY-MODIFIED CHARGE TRANSPORT COMPOUND HAVING AN AZINE GROUP

FIELD OF THE INVENTION

This invention relates to organophotoreceptors suitable for use in electrophotography and, more specifically, to organophotoreceptors having an improved charge transport compound having at least one azine group.

BACKGROUND OF THE INVENTION

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or solid toner is then provided in the vicinity of the latent image, and toner droplets or particles deposit in the vicinity of either the charged or uncharged areas to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are present in the element in separate layers, each of which can optionally be combined with a polymeric binder, deposited on the electrically conductive substrate. Two arrangements are possible. In one two-layer arrangement (the "dual layer" arrangement), the charge-generating layer is deposited on the electrically conductive substrate and the charge transport layer is deposited on top of the charge generating layer. In an alternate two-layer arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers, generally holes, and transport them through the charge transport layer in order to facilitate discharge of a surface charge on the photoconductive element. The charge transport material can be a charge transport compound, an electron transport compound, or a combination of both. When a charge transport compound is used, the charge transport compound accepts the hole carriers and transports them through the layer with the charge transport compound. When an electron transport compound is used, the electron transport compound accepts the electron carriers and transports them through the layer with the electron transport compound.

SUMMARY OF THE INVENTION

This invention provides organophotoreceptors having good electrostatic properties such as high $V_{acc}$ and low $V_{dis}$.

In a first aspect, an organophotoreceptor comprises an electrically conductive substrate and a photoconductive element on the electrically conductive substrate, the photoconductive element comprising:

a) a charge transport compound having the formula

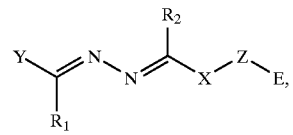

where $R_1$ and $R_2$ are, independently, hydrogen, an alkyl group, a heteocyclic group, an alkaryl group or an aryl group; X is an aromatic group; Y is an (N,N-disubstituted) arylamine group, such as a (N,N-disubstituted) arylamine group, a carbazole group or a julolidine group; Z is $(CH_2)_m$ group where m is an integer between 1 and 30 where one or more of the methylene groups is optionally replaced by O, S, C=O, O=C—O, O=C—NR$_3$, sulfoxide, sulfate, phosphate, an aryl group, urethane, urea, a NR$_4$ group, a CHR$_5$ group, or a CR$_6$R$_7$ group where $R_3$, $R_4$, $R_5$, $R_6$, and $R_7$ are, independently, H, hydroxyl, thiol, an amine group, an alkyl group, a heteocyclic group, an alkaryl group, or an aryl group; and E is an epoxy group; and (b) a charge generating compound.

The organophotoreceptor may be provided in the form of a plate, a flexible belt, a flexible disk, a sheet, a rigid drum, or a sheet around a rigid or compliant drum. In one embodiment, the organophotoreceptor includes: (a) a photoconductive element comprising the charge transport compound, the charge generating compound, the electron transport compound, and a polymeric binder; and (b) the electrically conductive substrate.

In a second aspect, the invention features an electrophotographic imaging apparatus that comprises (a) a light imaging component; and (b) the above-described organophotoreceptor oriented to receive light from the light imaging component. The apparatus can further comprise a liquid toner dispenser. The method of electrophotographic imaging with photoreceptors containing the above noted charge transport compounds is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a charge transport compound having the general formula (1) above.

The invention provides suitable charge transport compounds for organophotoreceptors featuring a combination of good mechanical and electrostatic properties. These photoreceptors can be used successfully with liquid toners to produce high quality images. The high quality of the imaging system can be maintained after repeated cycling.

Other features and advantages of the invention will be apparent from the following description of the particular embodiments thereof, and from the claims.

DETAILED DESCRIPTION OF PREFERRED EMBODIMENTS

Desirable charge transport compound are described herein having an azine group and an epoxy group. These charge transport compounds have desirable properties as evidenced by their performance in organophotoreceptors for electrophotography. In particular, the charge transport compounds of this invention have high charge carrier mobilities and good compatibility with various binder materials, can be cross-linked in both the single and multilayer photoconductive elements, and possess excellent electrophotographic properties. The organophotoreceptors according to this invention generally have a high photosensitivity, a low residual potential, and a high stability with respect to cycle testing, crystallization, and organophotoreceptor bending and stretching. The organophotoreceptors are particularly useful in laser printers and the like as well as photocopiers, scanners and other electronic devices based on electrophotography. The use of these charge transport compounds is described in more detail below in the context of laser printer use, although their application in other devices operating by electrophotography can be generalized from the discussion below.

To produce high quality images, particularly after multiple cycles, it is desirable for the charge transport compounds to form a homogeneous solution with the polymeric binder and remain approximately homogeneously distributed through the organophotoreceptor material during the cycling of the material. In addition, it is desirable to increase the amount of charge that the charge transport material, such as a charge transport compound, can accept (indicated by a parameter known as the acceptance voltage or "$V_{acc}$"), and to reduce retention of that charge upon discharge (indicated by a parameter known as the discharge voltage or "$V_{dis}$").

There are many charge transport compounds available for electrophotography. Examples of charge transport compounds include, for example, pyrazoline derivatives, fluorene derivatives, oxadiazole derivatives, stilbene derivatives, hydrazone derivatives, carbazole hydrazone derivatives, triaryl amines, polyvinyl carbazole, polyvinyl pyrene, polyacenaphthylene, or multi-hydrazone compounds comprising at least two hydrazone groups and at least two groups selected from the group consisting of p-(N,N-disubstituted) arylamine such as triphenylamine and heterocycles such as carbazole, julolidine, phenothiazine, phenazine, phenoxazine, phenoxathiin, thiazole, oxazole, isoxazole, dibenzo(1,4)dioxine, thianthrene, irnidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, cinnoline, diethylaminobenzene, and other substituted naphthalenes and benzenes. However, there is a need for other charge transport compounds to meet the various requirements of particular electrophotography applications.

In electrophotography applications, a charge-generating compound within an organophotoreceptor absorbs light to form electron-hole pairs. These electron-hole pairs can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport compounds described herein are especially effective at transporting charge, and in particular holes from the electron-hole pairs formed by the charge generating compound. In some embodiments, a specific electron transport compound can also be used along with the charge transport compound.

The layer or layers of materials containing the charge generating compound and the charge transport compounds are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport compound can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport compound and a polymeric binder; (b) a charge generating layer comprising the charge generating compound and a polymeric binder, and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport compound and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor, (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

As described herein, an organophotoreceptor comprises a charge transport compound having the formula

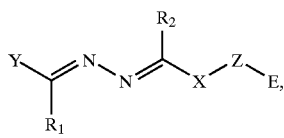

where $R_1$ and $R_2$ are, independently, hydrogen, an alkyl group, a heterocyclic group, an alkaryl group or an aryl group; X is an aromatic group; Y is an (N,N-disubstituted) arylamine group; Z is $(CH_2)_m$ group where m is an integer between 1 and 30 where one or more of the methylene groups is optionally replaced by O, S, C=O, O=C—O, O=C—$NR_3$, sulfoxide, sulfate, phosphate, an aryl group, urethane, urea, a $NR_4$ group, a $CHR_5$ group, or a $CR_6R_7$ group where $R_3$, $R_4$, $R_5$, $R_6$, and $R_7$ are, independently, H, hydroxyl, thiol, an amine group, an alkyl group, a heterocyclic group, an alkaryl group, or an aryl group; and E is an epoxy group, i.e. an epoxide group.

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The term group indicates that the generically recited chemical entity (e.g., alkyl group, phenyl group, julolidine group, (N, N-disubstituted) arylamine group, etc.) may have any substituent thereon which is consistent with the bond structure of that group. For example, where the term 'alkyl group' is used, that term would not only include unsubstituted liner, branched and cyclic alkyls, such as methyl, ethyl, isopropyl, tert-butyl, cyclohexyl, dodecyl and the like, but also substituents such as hydroxyethyl, cyanobutyl, 1,2,3-trichloropropane, and the like. However, as is consistent with such nomenclature, no substitution would be included within the term that would alter the fundamental bond structure of the underlying group. For example, where a phenyl group is recited, substitution such as 1-hydroxyphenyl, 2,4-fluorophenyl, orthocyanophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Similarly, when referring to carbazole group or julolidine group, the compound or substituent cited will include any substitution that does not substantively alter the chemical nature of the carbazole ring or the julolidine ring in the formula. When referring to an (N, N-disubstituted) arylamine group, the two substituents attached to the nitrogen may be any group that will not substantively alter the chemical nature of the amine group. Where the term moiety is used, such as alkyl moiety or phenyl moiety, that terminology indicates that the chemical material is not substituted. Where the term alkyl moiety is used, that term represents only an unsubstituted alkyl hydrocarbon group, whether branched, straight chain, or cyclic.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport compound and a charge generating compound in a polymeric binder, which may or may not be in the same layer, as well as an electron transport compound in some embodiments. For example, the charge transport compound and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (Stabar™ S-100, available from ICI), polyvinyl fluoride (Tedlar®, available from E.I. DuPont de Nemours & Company), polybisphenol-A polycarbonate (Makrofol™, available from Mobay Chemical Company) and amorphous polyethylene terephthalate (Melinar™, available from ICI Americas, Inc.). The electrically conductive materials may be graphite, dispersed carbon black, iodide, conductive polymers such as polypyroles and Calgon® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness of from about 0.5 mm to about 2 mm.

The charge generating compound is a material that is capable of absorbing light to generate charge carriers, such as a dye or pigment. Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygalliuin phthalocyanine, squarylium dyes and pigments, hydroxy-substituted squarylium pigments, perylimides, polynuclear quinones available from Allied Chemical Corporation under the tradename Indofast® Double Scarlet, Indofast® Violet Lake B, Indofast® Brilliant Scarlet and Indofast® Orange, quinacridones available from DuPont under the tradename Monastral™ Red, Monastral™ Violet and Monastral™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may contain an electron transport compound. Generally, any electron transport compound known in the art can be used. Non-limiting examples of suitable electron transport compound include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno4H-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethyl-idene)thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenyl idene)malononitrile, (4-carbitoxy-9-fluorenylidene)malononitrile, and diethyl(4-n-butoxy carbonyl-2,7-dinitro-9-fluorenylidene)-malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxycarbonyl)methylene]anthrone, 1,8-dihydroxy-10-[bis(ethoxycarbonyl)methylene]anthrone, and 1-cyano-10-[bis(ethoxycarbonyl)methylene]anthrone, 7-nitro-2-aza-9-fluroenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinoedimethane, 2,4,5,7-tetranitro-9-fluorenone, 2,4,7-trinitro-9-dicyanomethylene fluorenone, 2,4,5,7-tetranitroxanthone derivatives, and 2,4,8-trinitrothioxanthone derivatives. In some embodiments of interest, the electron transport compound comprises an (alkoxycarbonyl-9-fluorenylidene) malononitrile derivative, such as (4-n-butoxycarbonyl-9-fluorenylidene)malononitrile.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the WV stabilizers with electron transport compounds, the particular advantages of the UV stabilizers may not be their UV stabilizing abilities, although the UV stabilizing ability may be further advantageous in reducing degradation of the organophotoreceptor over time. While not wanting to be limited by theory, the synergistic relationship contributed by the UV stabilizers may be related to the electronic properties of the compounds, which contribute to the UV stabilizing function, by further contributing to the establishment of electron conduction pathways in combination with the electron transport compounds. In particular, the organophotoreceptors with a combination of the electron transport compound and the UV stabilizer can demonstrate a more stable acceptance voltage $V_{acc}$ with cycling. The improved synergistic performance of organophotoreceptors with layers comprising both an electron transport compound and a UV stabilizer are described further in copending U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as Tinuvin 144 and Tinuvin 292 (from Ciba Specialty Chemicals, Terrytown, N.Y.), hindered alkoxydialkylamines such as Tinuvin 123 (from Ciba Specialty Chemicals), benzotriazoles such as Tinuvan 328, Tinuvin 900 and Tinuvin 928 (from Ciba Specialty Chemicals), benzophenones such as Sanduvor 3041 (from Clariant Corp., Charlotte, N.C.), nickel compounds such as Arbestab (from Robinson Brothers Ltd, West Midlands, Great Britain), salicylates, cyanocinnamates, benzylidene malonates, benzoates, oxanilides such as Sanduvor VSU (from Clariant Corp., Charlotte, N.C.), triazines such as Cyagard UV-1164 (from Cytec Industries Inc., N.J.), polymeric sterically hindered amines such as Luchem (from Atochem North America, Buffalo, N.Y.). In some embodiments, the light stabilizer is selected from the group consisting of hindered trialkylamines having the following formula:

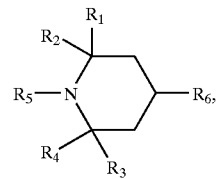

-continued

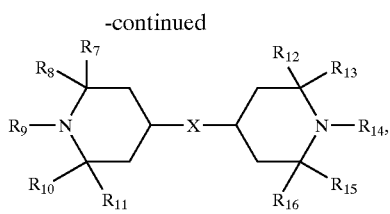

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, independently, hydrogen, alkyl group, or ester, or ether group; and $R_5$, $R_9$, and $R_{14}$ are, independently, alkyl group; and X is a linking group selected from the group consisting of —O—CO—$(CH_2)_m$—CO—O— where m is between 2 to 20.

The binder generally is capable of dispersing or dissolving the charge transport compound (in the case of the charge transport layer or a single layer construction), the charge generating compound (in the case of the charge generating layer or a single layer construction), and/or an electron transport compound for appropriate embodiments. Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. Suitable binders include, for example, polyvinyl butyral, such as BX-1 and BX-5 form Sekisui Chemical Co. Ltd., Japan.

Suitable optional additives for any one or more of the layers include, for example, antioxidants, coupling agents, dispersing agents, curing agents, surfactants, and combinations thereof.

The photoconductive element overall typically has a thickness from about 10 to about 45 microns. In the dual layer embodiments having a separate charge generating layer and a separate charge transport layer, charge generation layer generally has a thickness form about 0.5 to about 2 microns, and the charge transport layer has a thickness from about 5 to about 35 microns. In embodiments in which the charge transport compound and the charge generating compound are in the same layer, the layer with the charge generating compound and the charge transport composition generally has a thickness from about 7 to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent in further embodiments in an amount from about 1 to about 15 weight percent and in other embodiments in an amount from about 2 to about 10 weight percent, based on the weight of the photoconductive layer. The charge transport compound is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional electron transport compound, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount of from about 20 to about 75 weight percent, based on the weight of the charge generation layer. The optional electron transport compound in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport compound, the photoconductive layer generally comprises a binder, a charge transport compound, and a charge generation compound. The charge generation compound can be in an amount from about 0.05 to about 25 weight percent and in further embodiment in an amount from about 2 to about 15 weight percent, based on the weight of the photoconductive layer. The charge transport compound can be in an amount from about 10 to about 80 weight percent, in other embodiments from about 25 to about 65 weight percent, in additional embodiments from about 30 to about 60 weight percent and in further embodiments in an amount of from about 35 to about 55 weight percent, based on the weight of the photoconductive layer, with the remainder of the photoconductive layer comprising the binder, and optionally additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport compound may comprise an electron transport compound. The optional electron transport compound, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport layer can advantageously further include a UV light stabilizer. In particular, the electron transport layer generally can comprise an electron transport compound, a binder, and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any of one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, a charge transport compound, an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymner, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

An overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrolidone, polyurethane, polymethyl methacrylate, poly(hydroxy amino ether) and the like. Barrier and adhesive layers are described further in U.S. Pat.

No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, silicones, and the like. In some embodiments, the sub-layer has a dry thickness between about 20 Angstroms and about 2,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport compounds as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. patent applications Ser. Nos. 2002/0128349, entitled "Liquid Inks Comprising A Stable Organosol," 2002/0086916, entitled "Liquid Inks Comprising Treated Colorant Particles," and 2002/0197552, entitled "Phase Change Developer For Liquid Electrophotography," all three of which are incorporated herein by reference.

Charge Transport Compound

As described herein, an organophotoreceptor comprises a charge transport compound having the formula

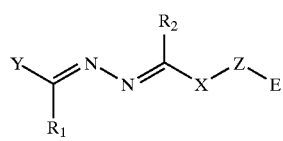

(1)

where $R_1$ and $R_2$ are, independently, hydrogen, an alkyl group, a heterocyclic group, an alkaryl group or an aryl group; X is an aromatic group; Y is a (N,N-disubstituted) arylamine group; Z is $(CH_2)_m$ group where m is an integer between 1 and 30 where one or more of the methylene groups is optionally replaced by O, S, C=O, O=C—O, O=C—$NR_3$, sulfoxide, sulfate, phosphate, an aryl group, urethane, urea, a $NR_4$ group, a $CHR_5$ group, or a $CR_6R_7$ group where $R_3$ $R_4$, $R_5$, $R_6$, and $R_7$ are, independently, H, hydroxyl, thiol, an amine group, an alkyl group, a heterocyclic group, an alkaryl group, or an aryl group; and E is an epoxy group. In some embodiments, X can be a phenylene group, a naphthalene group and an (N,N-disubstituted) aminophenylene group. In some embodiments of particular interest, m=2 and one ($CH_2$) group is replaced by O.

Specific, non-limiting examples of suitable charge transport compounds within the general Formula (1) of the present invention have the following structures.

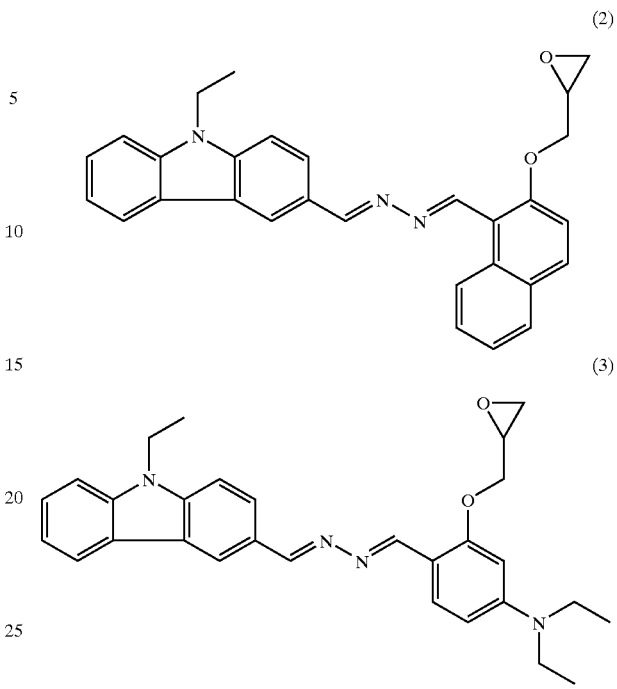

Synthesis of Charge Transport Compounds

The synthesis of the charge transport compounds with an azine group, as described herein, can be based on hydrazine, such as hydrazine monohydrate, which is available from Aldrich (Milwaukee, Wis.). Specifically, the charge transport compounds described herein can be synthesized by reacting hydrazine monohydrate, with two substituted aldehydes/ketones. One of the aldehydes/ketones is an N,N-disubstituted amino aryl substituted aldehyde or ketone, which reacts with a hydrazine in an appropriate acid catalyzed reaction to form a hydrazone. This aldehyde or ketone provides the Y group and the $R_1$ in Formula (1). The other substituted aldehyde/ketone is a functionalized aromatic aldehyde or ketone, which similarly reacts with a hydrazine to form a hydrazone. This functionalized aromatic aldehyde or ketone is functionalized to provide a functional group that can be reacted to form the —Z—E group of the product charge transport compound, as described further below. Also, this functionalized aromatic aldehyde or ketone provides the X group and the $R_2$ group of Formula (1). The two aldehydes/ketones can be reacted sequentially to first form a hydrazone that is subsequently reacted to form the azine. In the first reaction to form the hydrazone, a significant excess of hydrazine can be used to reduce the formation of a symmetric azine rather than a selected asymmetric azine of formula (1) above based on the sequential reaction with two different aldehydes/ketones.

The azine that is formed can be reacted to form an epoxy derivatized compound. For example, the functionalized aromatic group can be functionalized with active hydrogens, such as a primary amino group, a secondary amino group, a hydroxyl group, or a mercapto group. The functionalized compound reacts with the epichlorohydrin by way of the active hydrogen, such as in a base catalyzed reaction, to form the epoxy group with a —$CH_2$— group (as the Z-group) between the epoxy group and the aromatic X group. While epichlorohydrin can be used to form the epoxy substituted compound with Z=—$CH_2$—, alternatively other Z groups can be formed, for example, using two functional groups, specifically, with a halogen and with a vinyl group (C=C) or substituted vinyl group. The halide group can be replaced by a bond to the group with the active hydrogen of the azine through a nucleophilic substitution. The vinyl or substituted vinyl group can be converted to the epoxy group in a epoxidation reaction, for example, by the reaction with perbenzoic acid or other peroxy acid, in an electrophilic addition reaction. Thus, the identity of Z can be selected as desired through the introduction of a difunctional compound with a halide group and a vinyltsubstituted-vinyl group.

Arylaldehydes

As noted above, two aryl aldehydes/ketones are reacted to form the charge transport compounds. One of the arylaldehydes or arylketones is a (N,N-disubstituted) arylamine aldehyde. Representative (N,N-disubstituted) arylamine aldehydes for reacting with the hydrazine can be obtained as follows. A wide range of aryl aldehydes can be used for the other aldehyde reactant, including a variety of commercially available compounds. Two representative commercially available arylaldehydes are described in the examples below.

Synthesis Of Julolidine Aldehyde

Julolidine (100 g, 0.6 moles, commercially obtained from Aldrich Chemicals Co, Milwaukee, Wis. 53201) was dissolved in dimethylformamide (DMF) (200 ml, commercially obtained from Aldrich) in a 500 ml three neck round bottom flask. The flask was cooled to 0° C. in ice bath. Phosphorus trichloride oxide (POCl$_3$) (107 g, 0.7 mole, Aldrich) was added drop wise while keeping the temperature below 5° C. After the addition of POCl$_3$ was completed, the flask was warmed to room temperature and placed in a steam bath while stirring for a period of 1 hour. The flask was cooled to room temperature and the solution was added slowly to a large excess of distilled water with good agitation. Stirring was continued for additional 2 hours. The solid was filtered off and washed repeatedly with water until the effluent water became neutral. The product was dried in vacuum oven at 50° C. for 4 hours.

Other Aryl Aldehydes

Suitable commercially available (N,N-disubstituted) arylamine aldehydes are available form Aldrich (Milwaukee, Wis.) including, for example, diphenylaminobenzaldehyde (($C_6H_5$)$_2$NC$_6$H$_4$CHO) and 9-ethyl-3-carbazolecarboxyaldehyde.

Synthesis of Hydrazones

A hydrazine can be reacted with an appropriate aromatic aldehyde/ketone to form a desired hydrazone. The reactions can be catalyzed by an appropriate amount of concentrated acid. After mixing in the catalytic amount of acid with the hydrazine and aromatic aldehyde, the mixture can be refluxed for about 2 hours to about 16 hours. The initial product can be purified by recrystallization. The synthesis of selected compounds from the formulas above are described below in the Examples, and the other compounds described herein can be similarly synthesized.

The invention will now be described further by way of the following examples.

EXAMPLES

Example 1

Synthesis of Charge Transport Compounds

This example describes the synthesis of two charge transport compounds corresponding to Formulas 2 and 3 above.

Compound (2)

A quantity of 98% hydrazine monohydrate (50 ml, 1.4 mole, obtained from Aldrich, Milwaukee, Wis.) and 10 ml of triethylamine (obtained from Aldrich, Milwaukee, Wis.) were added to a 250 ml, 2-neck round bottom flask equipped with a mechanical stirrer and an addition funnel. The solution was stirred vigorously at room temperature for a period of 10–15 min. A solution of 9-ethyl-3-carbazolecarboxyaldehyde (22.3 g, 0.1 mol, from Aldrich, Milwaukee, Wis.) in 30 ml of tetrahydrofuran (THF) were added slowly to the round bottom flask. After the addition of aldehyde was completed, the reaction mixture was stirred at room temperature for 2 hours. Then, the reaction mixture was diluted with 50 ml of water. A precipitate was collected by filtration and washed repeatedly with water to give crude, i.e. without further purification, 9-ethyl-3-carbazolecarboxyaldehyde hydrazone, which was used in the next step immediately.

The crude 9-ethyl-3-carbazolecarboxyaldehyde hydrazone (23.7 g, 0.1 mole, obtained in the previous step) were added to a refluxed solution of 2-hydroxy-1-naphthaldehyde (17.2 g, 0.1 mol, obtained from Aldrich, Milwaukee, Wis.) in 50 ml of dioxane. The reflux process was continued for 10–15 min, and then the reaction mixture was allowed to stand at room temperature. The crystals formed upon standing were filtered off and washed with 2-propanol and ether to give 38 g (for a yield of 97%) of the expected azine. The product was recrystallized from dioxane to yield a product with a melting point of 184–186° C. (from dioxane). The $^1$H-NMR spectrum (100 MHz, CDCl$_3$) showed the following chemical shifts (ppm): δ=13.5 (s, 1H, OH); δ=9.7 (s, 1H, one of CH=N); δ=8.8 (s, 1H, one of CH=N); δ=8.5 (s, 1H, 4-H Ht); δ=8.3–7.1 (m, 12H, Ar); δ=4.3 (q, J=7.1 Hz, 2H, NCH$_2$CH$_3$); δ=1.4 (t, 3H, J=7.1 Hz, NCH$_2$CH$_3$). An elemental analysis yielded in weight %: C=79.59; H=5.38; N=10.52, which compared to calculated values for $C_{26}H_{21}N_3O$ of (weight %): C=79.77; H=5.41; N=10.73.

The product azine (27.4 g, 0.07 mol, prepared in previous step) and epichlorohydrin (80 ml, 1 mol, obtained from Aldrich, Milwaukee, Wis.) were added to a 250 ml 3-neck round bottom flask equipped with a reflux condenser, a thermometer and a mechanical stirrer. The reaction mixture was stirred vigorously at 35–40° C. for 24 h. Six periodically delivered portions, powdered 85% potassium hydroxide (26.8 g, 0.4 mol) and anhydrous sodium sulphate (6.8 g, 0.05 mol), were added during the reaction time, and the reaction mixture was temporarily cooled to 20–25° C. prior to each addition. After the termination of the reaction, the mixture was cooled to room temperature and filtered. The organic phase was treated with ethyl acetate and washed with distilled water until the wash water was neutral. The organic layer was dried over anhydrous magnesium sulfate, treated with activated charcoal, and filtered. The solvent was removed. The residue was subjected to column chromatography (silica gel, grade 62, 60–200 mesh, 150 Å, Aldrich, Milwaukee, Wis.) using 1:4 by volume acetone: hexane as the eluant. Fractions containing the product were collected and evaporated to afford an oily residue that was dissolved in the 30 ml of methanol/toluene at a 1/1 volume ratio. The crystals formed upon standing were filtered off and washed with 2-propanol to give 18 g (for a 57% yield) of compound (2). The product had a melting point of 164.5–165.5° C. (from methanol/toluene, 1/1 volume ratio). The $^1$H-NMR spectrum (100 MHz, CDCl$_3$) showed the following chemical shifts (ppm): δ=9.5 (m, 1H, one of CH=N); δ=9.0 (s, 1H, one of CH=N); δ=8.6 (s, 1H, 4-HHt); δ=8.3–7.2 (m, 12H, Ar); δ=4.6–4.0 (m, 4H, OCH$_2$, NCH$_2$CH$_3$); δ=3.45 (m, 1H, CH); 2.9 (dd, 1H, one of CH$_2$ of oxirane); δ=2.7 (dd, 1H, one of CH$_2$ of oxirane); δ=1.4 (t, 3H, CH$_3$). An elemental analysis yielded in weight %: C=77.62; H=5.31; N=9.17, which compared with calculated values for C$_{29}$H$_{25}$N$_3$O$_2$ in weight % of: C=77.83; H=5.63; N=9.39.

Compound (3)

A quantity of 98% hydrazine monohydrate (50 ml, 1.4 mole, from Aldrich, Milwaukee, Wis.) and 10 ml of triethylamine (obtained from Aldrich, Milwaukee, Wis.) were added to a 250 ml, 2-neck round bottom flask equipped with a mechanical stirrer and an addition funnel. The solution was stirred vigorously at room temperature for 10–15 min. A solution of 9-ethyl-3-carbazolecarboxaldehyde (22.3 g, 0.1 mol, obtained from Aldrich, Milwaukee, Wis.) in 30 ml of THF was slowly added to the flask. After the addition of aldehyde was completed, the reaction mixture was stirred at room temperature for 2 hours. Then, the mixture was diluted with 50 ml of water. A precipitate was collected by filtration and washed repeatedly with water to give the crude, i.e. without further purification, 9-ethyl-3-carbazolecarboxaldehyde hydrazone, which was used in the next step immediately.

The crude 9-ethyl-3-carbazolecarboxaldehyde hydrazone (23.7 g, 0.1 mole, obtained in the previous step) was added to a refluxed solution of 4-diethylamino-2-hydroxybenzaldehyde (19.3 g, 0.1 mol, obtained from Aldrich, Milwaukee, Wis.) in 50 ml of dioxane. The reflux process was continued for 10–15 min, and then the dioxane was evaporated. The residue was dissolved in a solution of toluene (20 ml) and 2-propanol (20 ml), and the mixture was allowed to stand at room temperature overnight. The crystals formed upon standing were filtered off and washed with 2-propanol and ether to give 35 g (for a yield of 85%) of product azine. The product had a melting point of 177–179° C. (from toluene). The $^1$H-NMR spectrum (100 MHz, CDCl$_3$) showed the following chemical shifts (ppm): δ=12.2 (s, 1H, OH); δ=8.8 (s, 1H, CH=N); δ=8.7 (s, 1H, CH=N); δ=8.6 (s, 1H, 4-H Ht); δ=8.4–7.9 (dd, 2H, 1-H, 2-H of Ht); δ=7.6–7.1 (m, 5H, Ar); δ=6.3 (m, 2H, 3-H, 5-H of 1,2,4-subst. Ph); δ=4.4 (q, 2H, NCH$_2$CH$_3$); δ=3.5 (q, 4H, N(CH$_2$CH$_3$)$_2$); δ=1.5 (t, 3H, NCH$_2$CH$_3$); δ=1.4 (t, 6H,N (CH$_2$CH$_3$)$_2$). Elemental analysis yielded the following in weight %: C=75.59; H=6.68; N=13.52, which compared with calculated values for C$_{26}$H$_{28}$N$_4$O in weight % of: C=75.70; H=6.84; N=13.58.

The product azine (28.9 g, 0.07 mol, prepared in previous step) and epichlorohydrin (80 ml, 1 mol, commercially available from Aldrich, Milwaukee, Wis.) were added to a 250 ml 3-neck round bottom flask equipped with a reflux condenser, a thermometer and a mechanical stirrer. The reaction mixture was stirred vigorously at 35–40° C. for 24 h. In three periodically delivered portions, powdered 85% potassium hydroxide (13.4 g, 0.2 mol) and anhydrous sodium sulphate (3.4 g , 25 mmol) were added during the reaction process with prior temporary cooling of the reaction mixture to 20–25° C. After termination of the reaction, the mixture was cooled to room temperature and filtered. The organic phase was treated with ethyl acetate and washed with distilled water until the wash water was neutral. Then, the organic layer was dried over anhydrous magnesium sulfate, treated with activated charcoal, and filtered. The solvent was evaporated. The residue was subjected to column chromatography (silica gel, grade 62, 60–200 mesh, 150 Å, Aldrich) using 1:4 by volume acetone: hexane as the eluant. Fractions containing the product were collected and evaporated to afford solid residue that was recrystallized from toluene/ethyl acetate (1/5 volume ratio) to give 20 g (for a yield of 61%) of compound (3). The product had a melting point of 150–152° C. (from toluene/ethyl acetate, ⅕ volume ratio). The $^1$H-NMR spectrum (100 MHz, CDCl$_3$) showed the following chemical shifts (ppm): δ=9.1 (s, 1H, one of CH=N); δ=8.8 (s, 1H, one of CH=N); δ=8.5(s, 1H, 4-H Ht); δ=8.4–7.9 (m, 3H, 6-H of 1,2,4-subst. Ph, 1-H, 2-H, of Ht); δ=7.65–7.2 (m, 4H, Ht); δ=6.4(d, 1H, 5-H of 1,2,4-subst. Ph); δ=6.1 (m, 1H, 3-H of 1,2,4-subst. Ph); δ=4.64.0 (m, 4H, OCH$_2$, NCH$_2$CH$_3$); δ=3.6–3.2 (m, 5H, N(CH$_2$CH$_3$)$_2$, CH); δ=2.9 (dd, 1H, one of CH$_2$ of oxirane); δ=2.8 (dd, 1H, one of CH$_2$ of oxirane); δ=1.5(t, 3H, CH$_2$CH$_3$); δ=1.5 (t, 6H, N(CH$_2$CH$_3$)$_2$. Elemental analysis yielded in weight %: C=74.32; H=6.61; N=11.87, which compared with calculated values for C$_{26}$H$_{28}$N$_4$O in weight % of: C=74.33; H=6.88; N=11.96.

Example 2

Charge Mobility Measurements

This example describes the measurement of charge mobility for samples formed with the two charge transport compounds described in Example 1.

Sample 1

A mixture of 0.1 g of Compound 2 and 0.1 g of polycarbonate Z was dissolved in 2 ml of tetrahydrofuran (THF). The solution was coated on a polyester film with conductive aluminum layer by the dip roller method. After drying for 15 min. at an 80° C. temperature, a clear 10 μm thick layer was formed.

Sample 2

Sample 2 was prepared according to the procedure for Sample 1, except that Compound 3 was used in place of Compound 2.

Mobility Measurements

Each sample was corona charged positively up to a surface potential U, illuminated with 2 ns long nitrogen laser light pulse and the hole mobility μ was determined as described in Kalade et al., "Investigation of charge carrier transfer in electrophotographic layers of chalkogenide glasses," Proceeding IPCS 1994: The Physics and Chemistry of Imaging Systems, Rochester, N.Y., pp. 747–752, incorporated herein by reference. This hole mobility measurement was repeated changing the charging regime and charging the sample to different U values, which corresponded to different electric field strength inside the layer E. This dependence was approximated by the formula $$\mu = \mu_0 e^{\alpha\sqrt{E}}.$$

Here E is electric field strength, $\mu_0$ is the zero field mobility and α is Pool-Frenkel parameter. The mobility characterizing parameters $\mu_0$ and α values as well as the mobility value at the 6.4×10$^5$ V/cm field strength as determined from these measurements are given in Table 1.

TABLE 1

| Sample | $\mu_0$ (cm$^2$/V · s) | μ (cm$^2$/V · s) at 6.4 × 10$^5$ V/cm | α (cm/V)$^{1/2}$ |
|---|---|---|---|
| Compound (2) | — | 7.0 × 10$^{-7}$ | ~0.01 |
| Compound (3) | 7.4 × 10$^{-10}$ | 2.6 × 10$^{-7}$ | 0.0073 |

Example 3
Ionization Potential Measurements

This example describes the measurement of the ionization potential for the two charge transport compounds described in Example 1.

To perform the ionization potential measurements, a thin layer of charge transport compound about 0.5 μm thickness was coated from a solution of 2 mg of charge transport compound in 0.2 ml of tetrahydrofuran on a 20 cm² substrate surface. The substrate was polyester film with an aluminum layer over a methylcellulose sublayer of about 0.4 μm thickness.

Ionization potential was measured as described in Grigalevicius et al., "3,6-Di(N-diphenylamino)-9-phenylcarbazole and its methyl-substituted derivative as novel hole transporting amorphous molecular materials," Synthetic Metals 128 (2002), p. 127–131, incorporated herein by reference. In particular, each sample was illuminated with monochromatic light from the quartz monochromator with a deuterium lamp source. The power of the incident light beam was $2-5 \cdot 10^{-8}$ W. The negative voltage of −300 V was supplied to the sample substrate. The counter-electrode with the 4.5×15 mm² slit for illumination was placed at 8 mm distance from the sample surface. The counter electrode was connected to the input of the BK2-16 type electrometer, working in the open impute regime, for the photocurrent measurement. A $10^{-15}-10^{-12}$ amp photocurrent was flowing in the circuit under illumination. The photocurrent, I, was strongly dependent on the incident light photon energy hv. The $I^{0.5}$=f(hv) dependence was plotted. Usually the dependence of the square root of photocurrent on incident light quanta energy is well described by linear relationship near the threshold [see references "Ionization Potential of Organic Pigment Film by Atmospheric Photoelectron Emission Analysis," *Electrophotogranhy* 28, Nr. 4, p. 364 (1989) by E. Miyamoto, Y. Yamaguchi, and M. Yokoyama; and "Photoemission in Solids," Topics in Applied Physics, 26, 1–103 (1978) by M. Cordona and L. Ley, both of which are incorporated herein by reference]. The linear part of this dependence was extrapolated to the hv axis and Ip value was determined as the photon energy at the interception point. The ionization potential measurement has an error of ±0.03 eV. The ionization potential values are given in Table 2.

TABLE 2

| Compound | Ionization Potential $I_p$ (eV) |
|---|---|
| 2 | 5.69 |
| 3 | 5.27 |

As understood by those skilled in the art, additional substitution, variation among substituents, and alternative methods of synthesis and use may be practiced within the scope and intent of the present disclosure of the invention. The embodiments above are intended to be illustrative and not limiting. Additional embodiments are within the claims. Although the present invention has been described with reference to particular embodiments, will recognize that changes may be made in form and detail spirit and scope of the invention.

What is claimed is:

1. An organophotoreceptor comprising an electrically conductive substrate and a photoconductive element on the electrically conductive substrate, the photoconductive element comprising:

(a) a charge transport compound having the formula

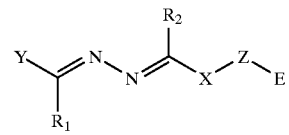

where $R_1$ and $R_2$ are, independently, hydrogen, an alkyl group, a heterocyclic group, an alkaryl group or an aryl group; X is an aromatic group; Y is an (N,N-disubstituted) arylamine group; Z is $(CH_2)_m$ group where m is an integer between 1 and 30 where one or more of the methylene groups is optionally replaced by O, S, C=O, O=C—O, O=C—$NR_3$, sulfoxide, sulfate, phosphate, an aryl group, urethane, urea, a $NR_4$ group, a $CHR_5$ group, or a $CR_6R_7$ group where $R_3$, $R_4$, $R_5$, $R_6$, and $R_7$ are, independently, H, hydroxyl, thiol, an amine group, an alkyl group, a heterocyclic group, an alkaryl group, or an aryl group; and E is an epoxy group; and (b) a charge generating compound.

2. An organophotoreceptor according to claim 1 wherein the (N,N-disubstituted) arylamine group is selected from the group consisting of p-(N,N-disubstituted)arylamine group, carbazole group, and julolidine group.

3. An organophotoreceptor according to claim 1 wherein the (N,N-disubstituted) arylamine group is a carbazole group.

4. An organophotoreceptor according to claim 1 wherein X is selected from the group consisting of phenylene group, naphthalene group, and (N,N-disubstituted)aminophenylene group.

5. An organophotoreceptor according to claim 1 wherein m=2 and one (CH₂) group is replaced by O.

6. An organophotoreceptor according to claim 1 wherein $R_1$ and $R_2$ are hydrogens.

7. An organophotoreceptor according to claim 1, wherein the charge transport compound has a formula selected from the group consisting of the following:

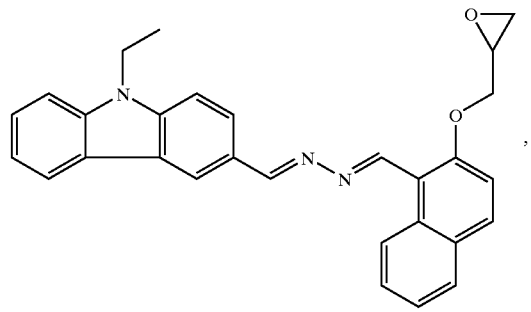

and

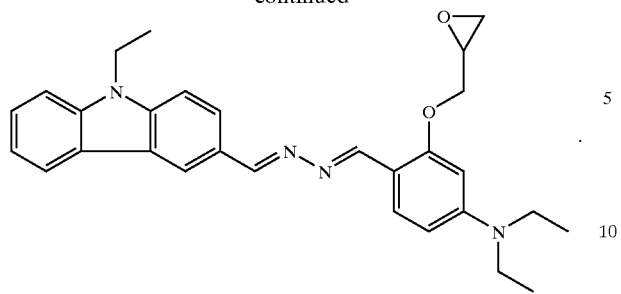

8. An organophotoreceptor according to claim 1 wherein the photoconductive element further comprises an electron transport compound.

9. An organophotoreceptor according to claim 1 wherein the photoconductive element further comprises a binder.

10. An electrophotographic imaging apparatus comprising:
(a) a light imaging component; and
(b) an organophotoreceptor oriented to receive light from the light imaging component, the organophotoreceptor comprising an electrically conductive substrate and a photoconductive element on the electrically conductive substrate, the photoconductive element comprising
(i) a charge transport compound having the formula

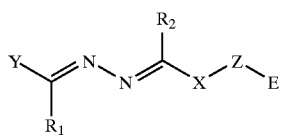

where $R_1$ and $R_2$ are, independently, hydrogen, an alkyl group, a heterocyclic group, an alkaryl group or an aryl group; X is an aromatic group; Y is an (N,N-disubstituted) arylamine group; Z is $(CH_2)_m$ group where m is an integer between 1 and 30 where one or more of the methylene groups is optionally replaced by O, S, C=O, O=C—O, O=C—$NR_3$, sulfoxide, sulfate, phosphate, an aryl group, urethane, urea, a $NR_4$ group, a $CHR_5$ group, or a $CR_6R_7$ group where $R_3$, $R_4$, $R_5$, $R_6$, and $R_7$ are, independently, H, hydroxyl, thiol, an amine group, an alkyl group, a heterocyclic group, an alkaryl group, or an aryl group, and E is an epoxy group; and (ii) a charge generating compound.

11. An electrophotographic imaging apparatus according to claim 10 wherein Y is selected from the group consisting of a p-(N,N-disubstituted)arylamine group, a carbazole group, and a julolidine group.

12. An electrophotographic imaging apparatus according to claim 10 wherein X is selected from the group consisting of phenylene group, naphthalene group, and (N,N-disubstituted)aminophenylene group.

13. An electrophotographic imaging apparatus according to claim 10 wherein m=2 and one of the $(CH_2)$ groups is replaced by O.

14. An electrophotographic imaging apparatus according to claim 10 wherein the charge transport compound has a formula selected form the group consisting of the following:

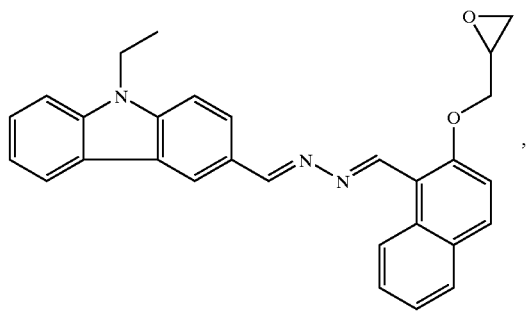

and

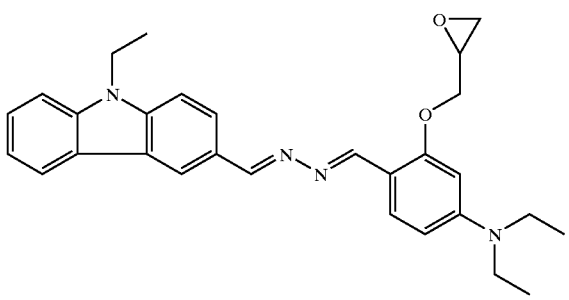

15. An electrophotographic imaging apparatus according to claim 10 wherein the photoconductive element further comprises an electron transport compound.

16. An electrophotographic imaging apparatus according to claim 10 wherein the photoconductive element further comprises a binder.

17. An electrophotographic imaging apparatus according to claim 10 further comprising a liquid toner dispenser.

18. An electrophotographic imaging process comprising:
(a) applying an electrical charge to a surface of an organophotoreceptor comprising an electrically conductive substrate and a photoconductive element on the electrically conductive substrate, the photoconductive element comprising
(i) a charge transport compound having the formula

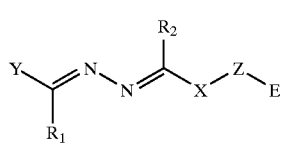

where $R_1$ and $R_2$ are, independently, hydrogen, an alkyl group, a heterocyclic group, an alkaryl group or an aryl group; X is an aromatic group; Y is an (N,N-disubstituted) arylamine group; Z is $(CH_2)_m$ group where m is an integer between 1 and 30 where one or more of the methylene groups is optionally replaced by O, S, C=O, O=C—O, O=C—$NR_3$, sulfoxide, sulfate, phosphate, an aryl group, urethane, urea, a $NR_4$ group, a $CHR_5$ group, or a $CR_6R_7$ group where $R_3$, $R_4$, $R_5$, &, and $R_7$ are, independently, H, hydroxyl, thiol, an amine group, an alkyl group, a heterocyclic group, an alkaryl group, or an aryl group, and E is an epoxy group; and (ii) a charge generating compound;
(b) imagewise exposing the surface of the organophotoreceptor to radiation to dissipate charge in selected areas and thereby form a pattern of charged and uncharged areas on the surface;
(c) contacting the surface with a toner to create a toned image; and
(d) transferring the toned image to a substrate.

19. An electrophotographic imaging process according to claim 18 wherein the (N,N-disubstituted) arylamine group is selected from the group consisting of a p-(N,N-disubstituted)arylamine group, a carbazole group, and a julolidine group.

20. An electrophotographic imaging process according to claim 19 wherein the (N,N-disubstituted) arylamine group is a carbazole group.

21. An electrophotographic imaging process according to claim 19 wherein the charge transport compound has a formula selected from the group consisting of the following:

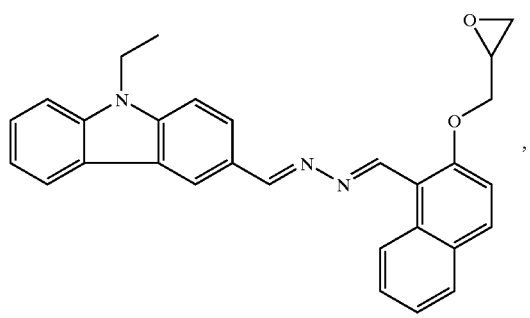

and

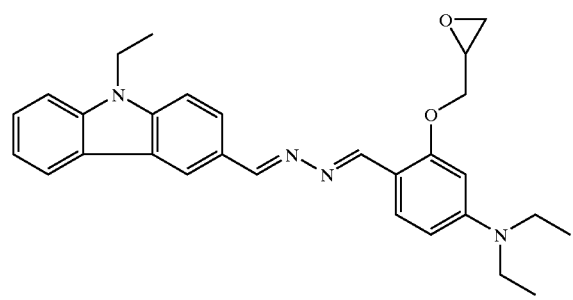

22. An electrophotographic imaging process according to claim 19 wherein the photoconductive element further comprises an electron transport compound.

23. An electrophotographic imaging process according to claim 19 wherein the photoconductive element further comprises a binder.

24. An electrophotographic imaging process according to claim 19 wherein the toner comprises a liquid toner comprising a dispersion of colorant particles in an organic liquid.

25. A charge transport compound having the formula

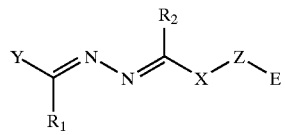

where $R_1$ and $R_2$ are, independently, hydrogen, an alkyl group, a heterocyclic group, an alkaryl group or an aryl group; X is an aromatic group; Y is an (N,N-disubstituted) arylamine group; Z is $(CH_2)_m$ group where m is an integer between 1 and 30 where one or more of the methylene groups is optionally replaced by O, S, C=O, O=C—O, O=C—$NR_3$, sulfoxide, sulfate, phosphate, an aryl group, urethane, urea, a $NR_4$ group, a $CHR_5$ group, or a $CR_6R_7$ group where $R_3$, $R_4$, $R_5$, $R_6$, and $R_7$ are, independently, H, hydroxyl, thiol, an amine group, an alkyl group, a heterocyclic group, an alkaryl group, or an aryl group, and E is an epoxy group.

26. A charge transport compound according to claim 25, wherein the (N,N-disubstituted) arylamine group is selected from the group consisting of a p-(N,N-disubstituted) arylamine group, a carbazole group, and a julolidine group.

27. A charge transport compound according to claim 25 wherein X is selected from the group consisting of phenylene group, naphthalene group, and (N,N-disubstituted) aminophenylene group.

28. A charge transport compound according to claim 25 wherein m=2 and one of the $(CH_2)$ groups is replaced by O.

29. A charge transport compound according to claim 25 wherein the (N,N-disubstituted) arylamine group is a carbazole group.

30. A charge transport compound according to claim 25 wherein the charge transport compound has a formula selected from the group consisting of the following:

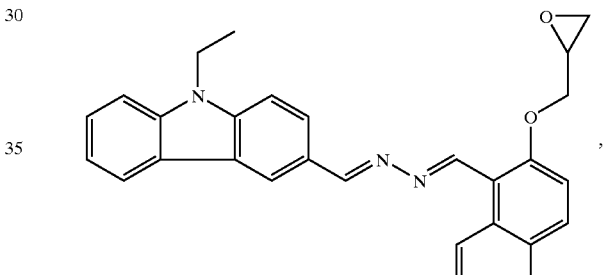

and

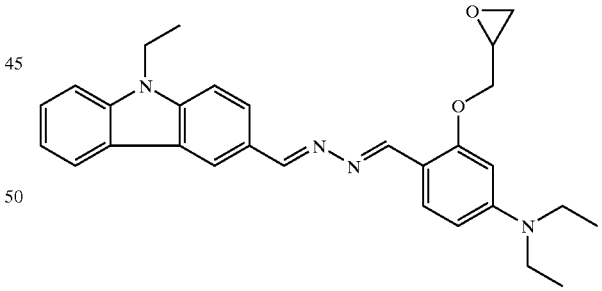

* * * * *